(12) United States Patent
Ellard et al.

(10) Patent No.: US 6,837,844 B1
(45) Date of Patent: Jan. 4, 2005

(54) SEED CARTRIDGE FOR RADIATION THERAPY

(75) Inventors: Terence R. Ellard, Seattle, WA (US); Stephen H. Knudsen, Bainbridge Island, WA (US)

(73) Assignee: Med-Tec Iowa, Inc., Orange City, IA (US)

(*) Notice: Subject to any disclaimer, the term of this patent is extended or adjusted under 35 U.S.C. 154(b) by 381 days.

(21) Appl. No.: 10/145,406

(22) Filed: May 14, 2002

(51) Int. Cl.[7] .......................... A61M 36/00; A61N 5/00
(52) U.S. Cl. ........................................... 600/7
(58) Field of Search ................ 600/1–8; 124/45, 124/48, 51.152, 63–68; 89/33.01, 33.02, 33.1

(56) References Cited

U.S. PATENT DOCUMENTS

| | | | |
|---|---|---|---|
| 4,086,914 A | | 5/1978 | Moore |
| 4,150,766 A | * | 4/1979 | Westendorf et al. ......... 221/112 |
| 4,167,179 A | | 9/1979 | Kirsch |
| 4,332,097 A | * | 6/1982 | Taylor, Jr. ...................... 42/50 |
| 4,451,254 A | * | 5/1984 | Dinius et al. .................. 604/62 |
| 4,692,628 A | | 9/1987 | Sauerwein et al. |
| 4,700,692 A | | 10/1987 | Baumgartner |
| 4,815,449 A | | 3/1989 | Horowitz |
| 4,986,251 A | * | 1/1991 | Lilley ........................... 124/67 |
| 5,242,373 A | | 9/1993 | Scott et al. |
| 5,460,592 A | | 10/1995 | Langton et al. |
| 5,522,797 A | | 6/1996 | Grimm |
| 5,561,698 A | | 10/1996 | Mick et al. |
| 5,799,432 A | * | 9/1998 | Wright et al. ................ 42/1.02 |
| 5,860,909 A | | 1/1999 | Mick et al. |
| 5,928,130 A | | 7/1999 | Schmidt |
| 6,099,457 A | | 8/2000 | Good |
| 6,102,844 A | | 8/2000 | Ravins et al. |
| 6,221,003 B1 | | 4/2001 | Sierocuk et al. |
| 6,267,718 B1 | | 7/2001 | Vitali et al. |
| 6,358,195 B1 | | 3/2002 | Green et al. |
| 2002/0049411 A1 | | 4/2002 | Lamoureux et al. |

FOREIGN PATENT DOCUMENTS

WO PCT WO 01/66185 A1 9/2001

* cited by examiner

*Primary Examiner*—Samuel G. Gilbert
(74) *Attorney, Agent, or Firm*—McKee, Voorhees & Sease, P.L.C.

(57) ABSTRACT

A large capacity seed cartridge is provided for a radiation therapy seed applicator. The seed cartridge is adapted for use with the Mick applicator, or other conventional applicators. The cartridge includes a housing with a seed drum mounted therein. A seed track extends around the seed drum. A spring operatively urges the seed in the track towards a discharge opening in the seed drum. A seed pusher rod in the applicator pushes each seed out of the opening and into the needle which is positioned in the patient, such that the seed is implanted into the body of a patient. The seed cartridge can be quickly and easily installed in the applicator and holds 120 radioactive seeds, or more.

10 Claims, 7 Drawing Sheets

SEED CARTRIDGE FOR RADIATION THERAPY

BACKGROUND OF THE INVENTION

Radiation therapy includes several different procedures, one of which is the implantation of radioactive seeds, such as iodine or palladium, into the patient's body adjacent the cancerous cells. Normally, the seeds are implanted at spaced positions in the body using a seed applicator. One common applicator is known as a Mick applicator. Various types of seed cartridges carrying multiple radioactive seeds have been designed for use with the Mick applicator and other applicators. However, these prior art seed cartridges typically only hold a small number of seeds, and thus must be changed or reloaded at frequent intervals, which involves more time and expense.

Accordingly, a primary objective of the present invention is the provision of an improved seed cartridge to hold and dispense a large quantity of radioactive seeds.

A further objective of the present invention is the provision of a seed cartridge adapted to mount in various seed applicators, including a Mick applicator.

Another objective of the present invention is the provision of an improved seed/spacer dispenser for radiation therapy which includes a seed cartridge and a spacer cartridge used for loading implant needles.

Still another objective of the present invention is the provision of a radiation seed applicator which can selectively implant both seeds and spacers into a patient's body.

These and other objectives become apparent from the following description of the invention.

SUMMARY OF THE INVENTION

The improved seed cartridge for holding and dispensing a large quantity of seeds for radiation therapy comprises a casing, with a seed drum within the casing. An elongated track is formed within the drum for holding the seeds. A spring is mounted in the casing to urge the seeds towards the discharge end of the drum. A hole extends through the discharge end through which a push rod of the applicator is insertable to push a seed into the applicator needle.

In a second embodiment, a seed cartridge assembly is provided for dispensing both seeds and spacers for radiation therapy. The assembly includes a body, with a needle interfaced for quickly attaching and detaching from the needle hub. A bore extends through the body. A push rod slidably extends into the bore and is movable between a retracted position withdrawn from the needle and an extended position in the needle. A seed cartridge having a plurality of seeds is mounted in the body with the discharge opening aligned with the push rod. A spacer cartridge is also mounted in the body and has a plurality of spacers loaded therein for ejection by the push rod into the needle. The seed cartridge and spacer cartridge are selectively positioned for alignment with the push rod such that either a seed or a spacer can be dispensed from the applicator needle.

DETAILED DESCRIPTION OF THE INVENTION

Figure 1:
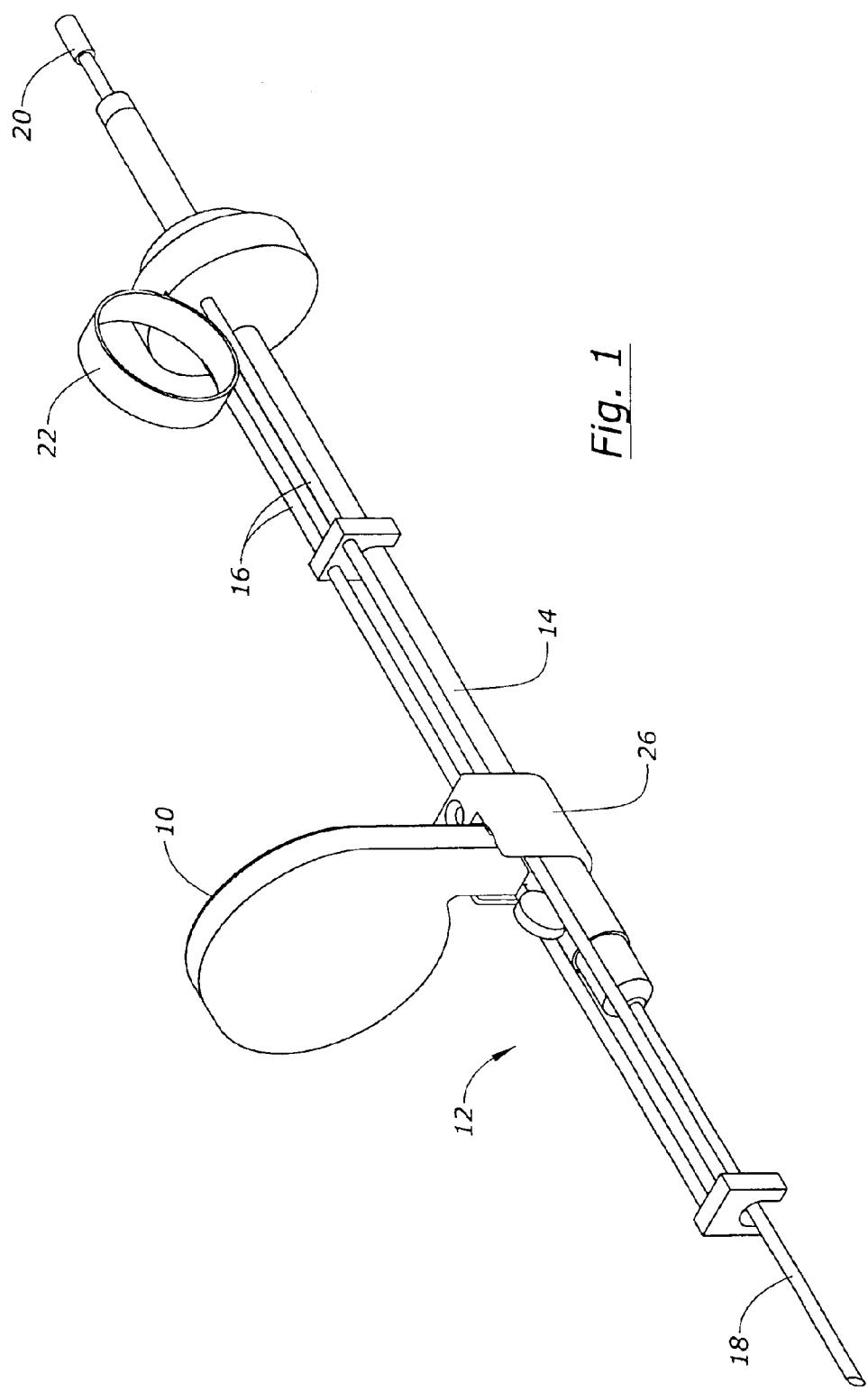
FIG. 1 is a perspective view of a seed applicator with the seed cartridge of the present invention mounted therein.

FIG. 1 shows the seed cartridge 10 of the present invention mounted in a conventional Mick applicator 12. The Mick applicator includes an elongated hollow barrel 14, structural support rods 16, a needle 18 extending from the outlet or downstream end of the barrel 14, and a push rod 20 extending into the upper or upstream end of the barrel 14. A thumb ring 22 facilitates holding of the applicator 12 during use.

Figure 2:
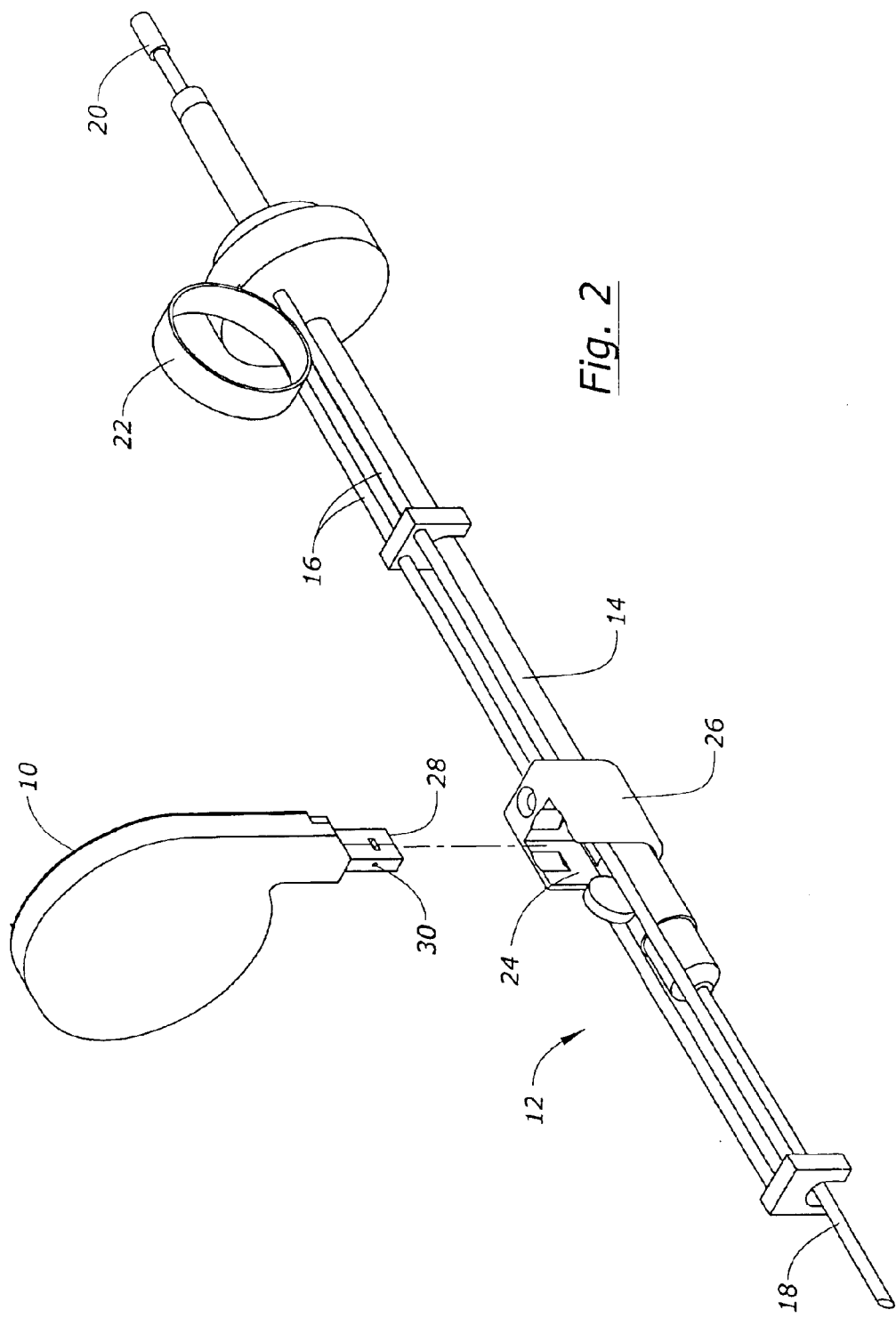
FIG. 2 is a view similar to FIG. 1 showing an exploded perspective view of the seed cartridge and applicator.

Adjacent the downstream end of the barrel 14 is a slot 24 in the upper portion of the barrel, as best seen in FIG. 2. A housing 26 having an open upper end extends around the barrel 14 and rods 16 adjacent the slot 24.

The above described structure of the Mick applicator 12 is conventional and does not constitute a part of the present invention.

The present invention is directed towards the seed cartridge 10 which is adapted to be received in the slot 24 of the Mick or other applicator barrel 14 to provide a large quantity (i.e. 120) of radioactive seeds for implantation into a patient's body via the needle 18. More particularly, the cartridge 10 has a lower end 28 adapted to slip into the slot 24. A hole 30 extends through the lower end 28 of the cartridge 10 and aligns with the longitudinal axis of the push rod 20. The radioactive seeds are loaded into the cartridge 10, such that the seeds will be sequentially presented to the hole 30 such that the push rod 20 can push each seed out of the hole 30 and into the needle 18 for implantation into the patient.

Figure 3:
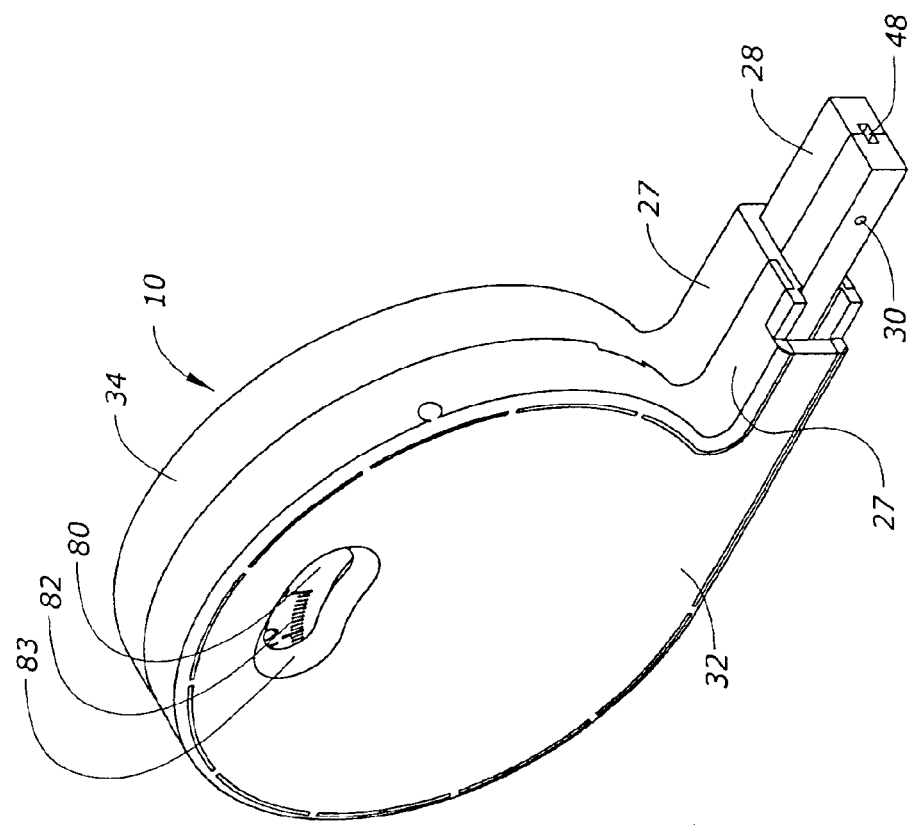
FIG. 3 is a perspective view of the seed cartridge.
Figure 4:
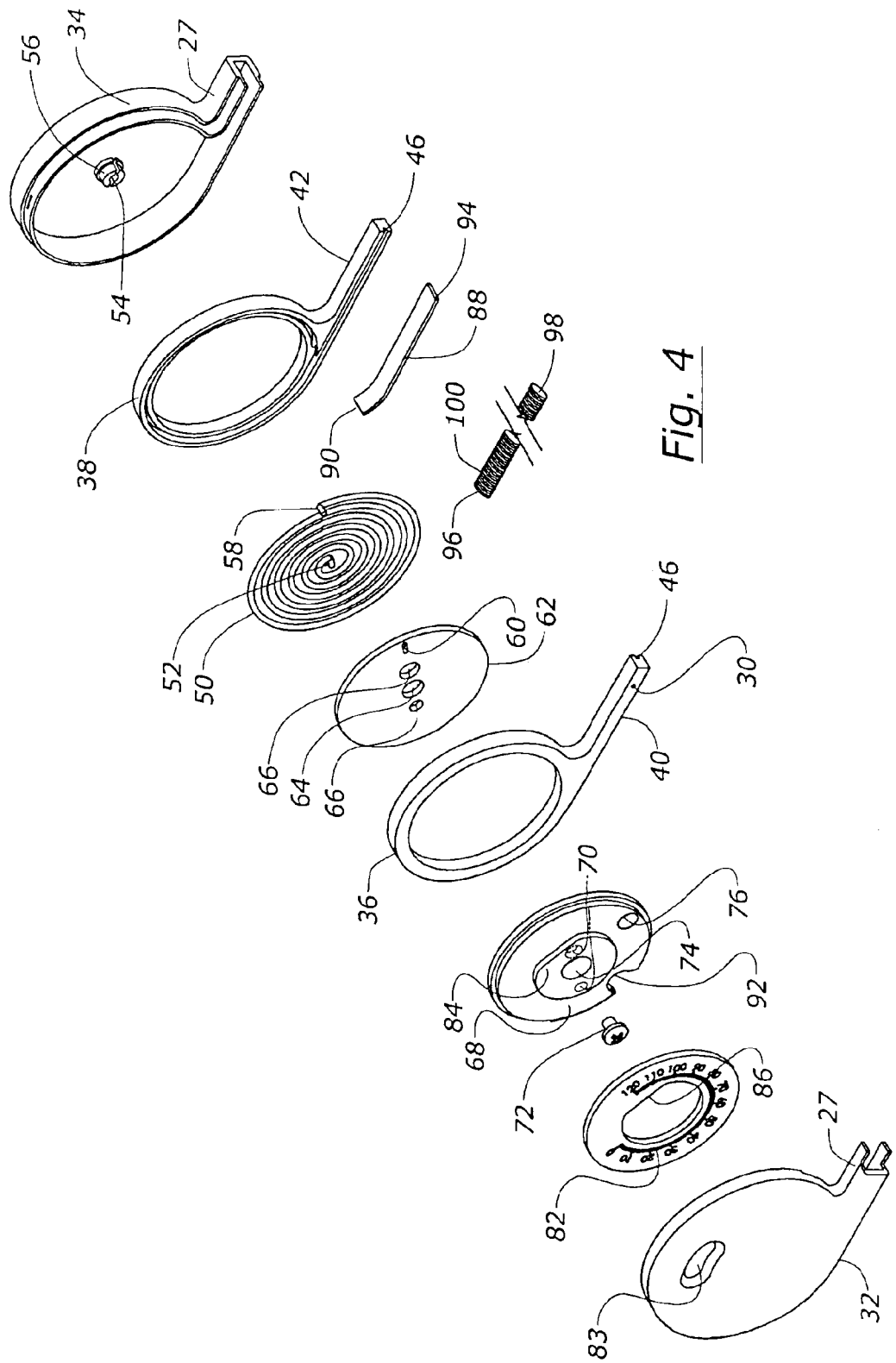
FIG. 4 is an enlarged view of the seed cartridge taken along lines 44 of FIG. 3.
Figure 5:
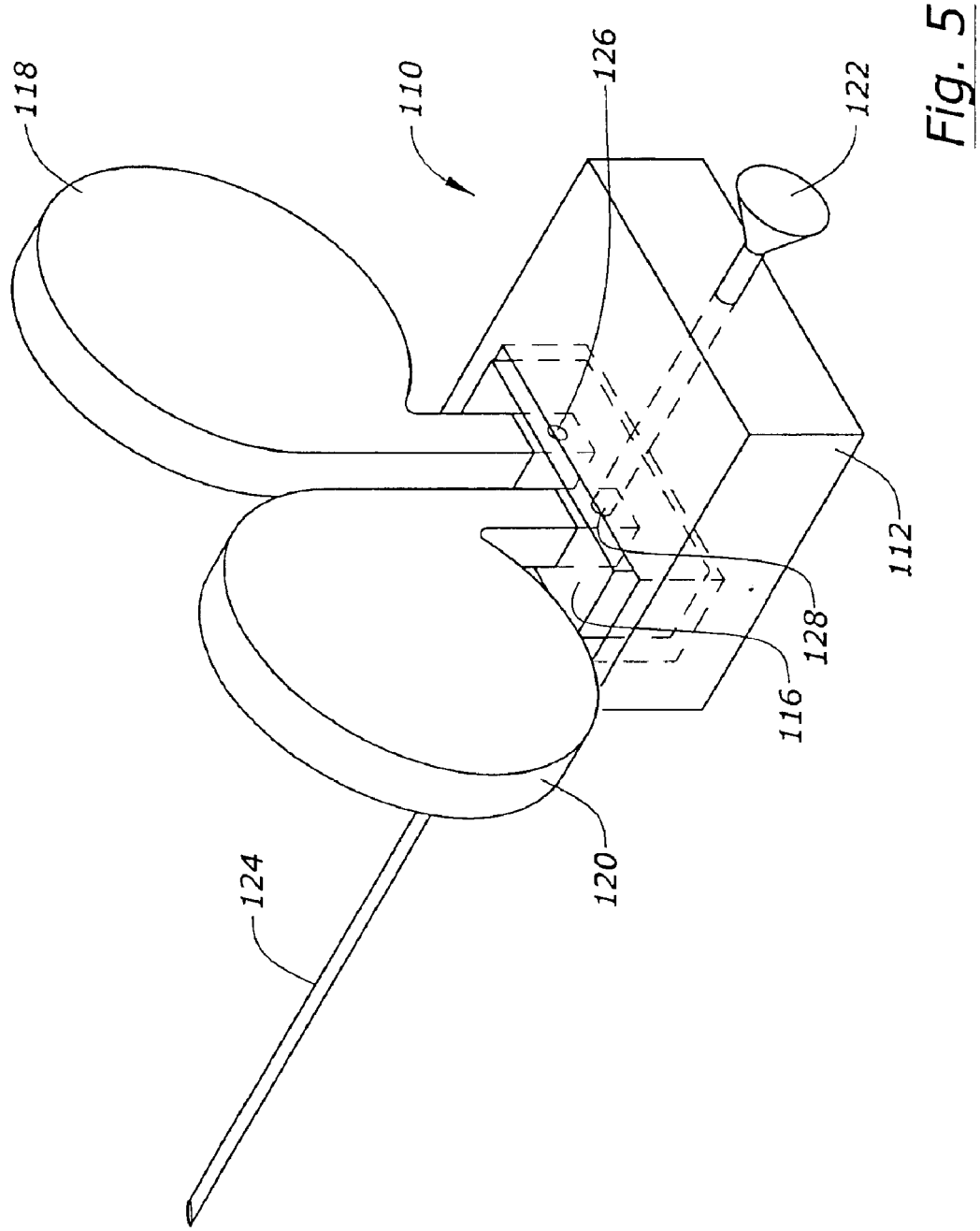
FIG. 5 is an exploded view of the components of the seed cartridge.

As best seen in FIG. 5, the seed cartridge 10 includes an upper casing 32 and a lower casing 34 which are adapted to frictionally fit together. Mounted within each casing 32, 34 is one-half of a drum body 36, 38, which are substantially mirror images of one another. Each drum body is generally circular, with a tangentially extending leg 40, 42. A slot 46 is formed within each drum body 36, 38, such that when the bodies 36, 38 are joined, an internal seed track storage is defined upstream from the hole. The hole 30 is formed in each of the legs 40, 42 of the drum bodies 36, 38, and resides outside of the leg 27 of the housing 26. A slot 48 extends downstream from the hole 30 to the end of the legs 40, 42 in each drum body 36, 38 to define a second track 49. Thus, the discharge opening 30 is spaced upstream from the distal end of the drum, as best seen in FIG. 3. The depth of slots 48 is less than the depth of slots 46, such that the second track is narrower than the storage track with a step 51 formed at the juncture of the tracks or adjacent holes 30. The second track 49 downstream from the holes 30 may be used in loading seeds into the primary seed storage track 47. For example, seeds may be loaded through the hole 30 and pushed upstream into track 47 by a tool extending into track 49. The step 51 prevents the seeds from discharging through the track 49, since the length of the seeds is greater than the width of the track 49.

A spiral spring 50 is mounted within the cartridge 10. The inner end 52 of the spring 50 extends into a slot 54 in a hub 56 extending inwardly from the lower casing 34. The outer end 58 of the spring 50 is received within a slot 60 in a plate 62. The plate 62 includes a central apperture 64, and a pair of holes 66 on either side of the apperture 64. A drive disk 68 includes a pair of stub shafts 70 which are matingly received within the holes 66 of the plate 62 so as to fix the plate 62 and drive disk 68 together. A bolt 72 extends through a central apperture 74 in the drive disk 68, and through the appeture 64 in the plate 62 for threaded receipt in the hub 56, so as to mount the plate 62 and the drive disk 68 in the lower casing 34 and so as to secure the inner end 52 of the spring 50 in the slot 54 of the hub 56.

The drive disk 68 includes a hole 76 to receive the outer end 58 of the spring 50 extending through the slot 60 of the plate 62. The drive disk 68 also includes a reduced-diameter step 78 upon which is mounted an indicia dial 80. The dial 80 includes indicia or markings 82 to indicate the quantity of radioactive seeds within the cartridge 10. The drive disk 68 and the dial 80 have mating surfaces 84, 86 so that the drive disk 68 and the dial 80 rotate in unison.

The cartridge 10 also includes a seed pusher 88 mounted in the track 48. The first end 90 of the seed pusher 88 is received in a recess or cut out portion 92 of the drive disk 68. The second end 94 of the seed pusher 88 engages the last seed in the chain of seeds within the track 47.

The spring 50, which is operatively connected to the drive disk 68, is biased to expand, such that the drive disk 68 urges the seed pusher 88 in a counterclockwise direction in the track 48, so as to thereby move the lead seed 98 in the seed chain 100 towards the discharge hole 30 of the drum bodies 36, 38. The push rod 20 can then be pushed forwardly into an extended position extending through the hole 30 so as to push the lead seed 98 into the needle 18 and then into the body of the patient. After implantation of the seed 98, the push rod 20 is retracted from the needle 18 and the drum bodies 36, 38, such that the spring 50 urges the next seed in the seed chain 100 into position aligned with the hole 30 for implantation into the patient's body.

Figure 6:
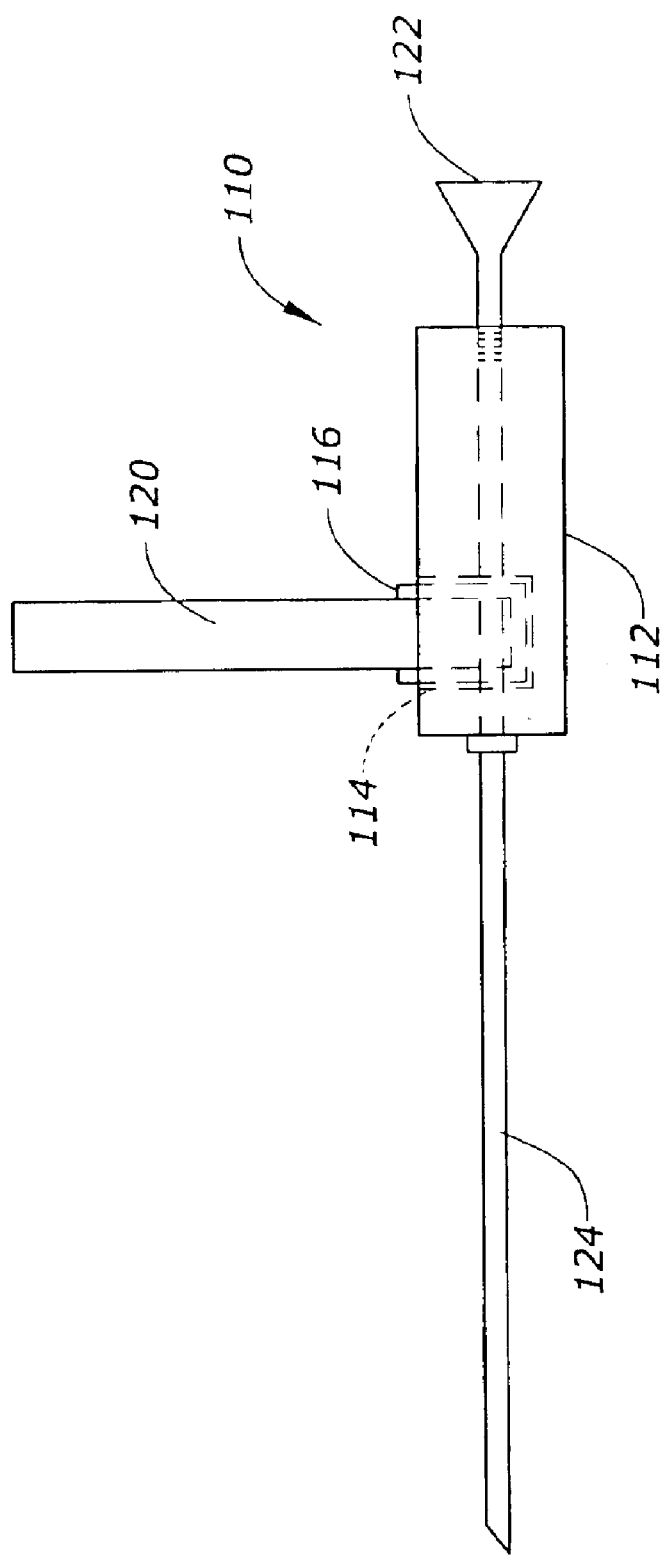
FIG. 6 is a view of an improved seed applicator assembly having both a seed cartridge and a spacer cartridge.
Figure 7:
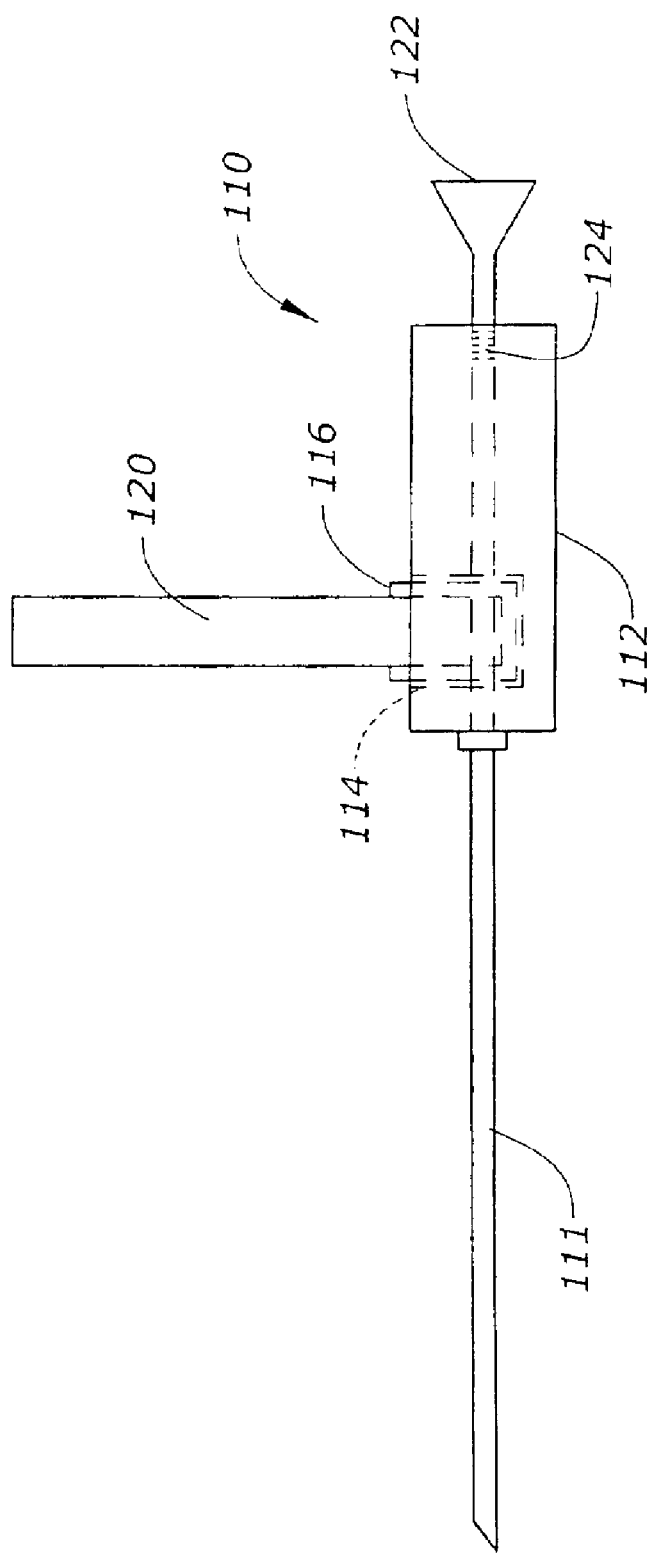
FIG. 7 is a side elevation view of the assembly of FIG. 5.

FIGS. 6 and 7 show a novel device 10 for loading seeds and spacers into a radiation therapy implant needle 111. The device 110 includes a base 112 having a recess 114 formed therein. The recess 114 is adapted to receive a slide block 116 which can slide from side to side within the recess 114. A seed cartridge 118, as described above, is adapted to fit into a first slot in the slide block 116. A spacer cartridge 120 is adapted to be received within a second slot in the slide block 116. The structure of the spacer cartridge 120 is identical to the structure of the seed cartridge 118. The main difference between the seed cartridge 118 and the spacer cartridge 120 is that the seed cartridge 118 is loaded with radiation seeds, whereas the spacer cartridge 120 is loaded with spacers. It is understood that the spacers are optional.

The base 112 includes an opening for receiving a pusher rod 122 on one side thereof, with the needle 111 extending from the other side of the base 112 opposite the pusher rod 122. The pusher rod 122 extends through discharge holes 126, 128, in the seed cartridge 118 and spacer cartridge 120, respectively. A spring 124 biases the pusher rod 122 to a retracted position.

In operation, the operator can slide the block 116 to the left (as seen in FIG. 5) in the slide block recess 114 such that a seed can be dispensed from the seed cartridge 118 and loaded into the needle 111 when the pusher rod 122 extends through the hole 126. The operator can then retract the pusher rod, slide the slide block 116 to the right side of the recess 114 in the base 112, and then extend the pusher rod 122 through the hole 128 in the spacer cartridge 120 so as to load a spacer into the needle 111. The seeds and spacers can be alternatively loaded, or multiple seeds or spacers can be sequentially loaded into the needle 111.

The loaded needle 111 can then be inserted into a patient or disengaged from the base 112 and installed on an applicator, such as a Mick applicator, for implanting the seeds and/or spacers into the patient. In this method, the needle 111 is pre-loaded before insertion into the patient. In conventional procedures, the needle is empty when inserted into the patient, and then seeds are loaded into the needle for implantation into the patient.

Whereas the invention has been shown and described in connection with the preferred embodiment thereof, it will be understood that any modifications, substitutions, and additions may be made which are within the intended broad scope of the following claims. From the foregoing, it can be seen that the present invention accomplishes at least all of the stated objectives.

What is claimed is:

1. A cartridge for holding and dispensing seeds for radiation therapy comprising:
   a casing adapted to mount to a seed applicator;
   a seed drum in the casing having an elongated track adapted to hold seeds and a discharge opening spaced apart from a distal end of the seed drum;
   a spring mounted in the casing to move the seeds along the track towards the discharge opening of the drum;
   the discharge opening being adapted to receive a rod to push out a seed.

2. The cartridge of claim 1 wherein the track extends along a perimeter of the seed drum.

3. The cartridge of claim 1 wherein the track extends substantially in a circular path.

4. The cartridge of claim 1 wherein the sprig has a fixed end secured to the casing.

5. The cartridge of claim 1 further comprising a seed pusher slidably mounted within the track between the seeds and a disk drive rotatably mounted in the casing.

6. The cartridge of claim 1 further comprising a dial mounted within the casing and having indicia to indicate the quantity of seeds in the drum.

7. The cartridge of claim 6 wherein the casing has a window to display the indicia on the dial.

8. The cartridge of claim 6 wherein the dial is operatively connected to the spring.

9. The cartridge of claim 1 wherein the casing includes first and second pieces frictionally fit together to enclose the seed drum.

10. The cartridge of claim 1 wherein the discharge opening extends substantially perpendicular to the track.

* * * * *